United States Patent [19]

Bacher et al.

[11] Patent Number: 5,656,760
[45] Date of Patent: Aug. 12, 1997

[54] FLUORESCENT WHITENING AGENTS

[75] Inventors: Jean-Pierre Bacher, Buschwiller; Claude Eckhardt, Riedisheim, both of France; Dieter Reinehr, Kandern, Germany

[73] Assignee: Ciba-Geigy Corporation, Tarrytown, N.Y.

[21] Appl. No.: 530,975

[22] Filed: Sep. 20, 1995

[30] Foreign Application Priority Data

Sep. 21, 1994 [GB] United Kingdom ............ 9418958

[51] Int. Cl.⁶ ............ C07D 251/48; C07D 251/54; C07D 403/02
[52] U.S. Cl. ............ 544/193.2; 544/198; 544/209
[58] Field of Search ............ 544/198, 209, 544/193.2

[56] References Cited

U.S. PATENT DOCUMENTS

| | | | |
|---|---|---|---|
| 3,716,532 | 2/1973 | Tscharner et al. | 260/240.1 |
| 3,867,376 | 2/1975 | Guender et al. | 260/240 B |
| 3,951,965 | 4/1976 | Mengler et al. | 260/240 B |
| 3,954,740 | 5/1976 | Fringeli | 260/240 B |
| 4,005,026 | 1/1977 | Heath et al. | 252/89 |
| 4,025,507 | 5/1977 | Fleck et al. | 260/240 B |
| 4,468,341 | 8/1984 | Beyer | 252/301.23 |
| 4,605,511 | 8/1986 | Fringeli | 252/301.21 |
| 5,051,111 | 9/1991 | Anceschi et al. | 8/648 |
| 5,181,935 | 1/1993 | Reinert et al. | 8/442 |
| 5,356,443 | 10/1994 | Reinert et al. | 8/586 |
| 5,493,022 | 2/1996 | Kaul et al. | 544/193.2 |

FOREIGN PATENT DOCUMENTS

| | | |
|---|---|---|
| 0024380 | 3/1981 | European Pat. Off. . |
| 1313469 | 4/1973 | United Kingdom . |
| 1451735 | 10/1976 | United Kingdom . |
| 1512076 | 5/1978 | United Kingdom . |

OTHER PUBLICATIONS

Lee, Fluorescent Whitening Agents in Heavy Duty Liquid Detergents, J. Chem. Tech. Biotechnol., 1991, 50, pp. 301–319 1991.

*Primary Examiner*—Mukund J. Shah
*Assistant Examiner*—Deepak R. Rad
*Attorney, Agent, or Firm*—Kevin T. Mansfield

[57] ABSTRACT

The present invention provides a compound having the formula:

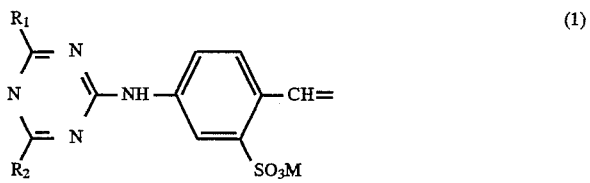

(1)

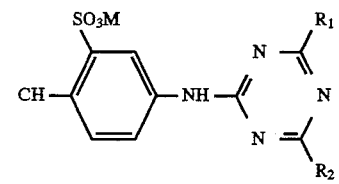

in which M is hydrogen, sodium, potassium, calcium, magnesium, ammonium, mono-, di-, tri- or tetra-$C_1$–$C_4$alkylammonium, mono-, di- or tri-$C_1$–$C_4$hydroxyalkylammonium or ammonium that is di- or tri-substituted by a mixture of $C_1$–$C_4$alkyl and $C_1$–$C_4$hydroxyalkyl groups; $R_1$ is a group having the formula:

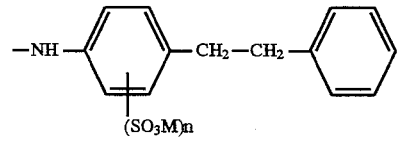

in which M has its previous significance and n is 1 or 2; and $R_2$ is O—$C_1$–$C_{12}$alkyl or $N(R_3)(R_4)$ in which $R_3$ and $R_4$, independently, are hydrogen, $C_1$–$C_{12}$alkyl or $C_1$–$C_4$hydroxyalkyl, or $R_3$ and $R_4$, together with the nitrogen atom, are the atoms required to form a pyrrolidine, piperidine or morpholine group.

The compounds of formula (1) are particularly useful as fluorescent whitening agents for cotton in discontinuous processes, in the course of which an acidic treatment, especially a finishing treatment using a polymer resin, occurs.

10 Claims, No Drawings

FLUORESCENT WHITENING AGENTS

The present invention relates to new fluorescent whitening agents and, in particular, to new diaminostilbene fluorescent whitening agents having good acid stability and high affinity to cotton.

Fluorescent whitening agents are widely used in the textile industry in order to improve the whiteness properties of a large range of textile fibre materials. With particular reference to cotton, care must be taken in the choice of fluorescent whitening agent and application technique, since fluorescent whitening agents exhibit a wide range of affinities for cotton.

In "batchwise" application methods, it is preferred to use fluorescent whitening agents which have a high affinity for cotton, since such fluorescent whitening agents exhibit a maximal exhaustion on to the cotton fibre from the bath.

For "continuous" processes, however, a fluorescent whitening agent of low affinity must be used, namely one which provides the same whiteness effect at the start of the material as at the end, since it exhausts only on to a minor proportion of the material.

In the case of certain other application methods, e.g. the "pad-batch" process, fluorescent whitening agents of intermediate affinity for cotton are required.

Moreover, fluorescent whitening agents are increasingly applied in discontinuous processes, in the course of which an acidic treatment, especially a finishing treatment using a polymer resin, occurs. In order to be effective in such processes, the fluorescent whitening agents used must exhibit a high fibre affinity. Unfortunately, however, the existing high affinity fluorescent whitening agents are stable only in the pH range which extends from alkaline to neutral values. Even at a pH value of only 6, the existing high affinity fluorescent whitening agents become turbid and form precipitates, with consequent reduction in their whitening effects. Moreover, in multistage processes, if such high affinity fluorescent whitening agents have already been applied in a first stage, when treated subsequently in an acid bath, they undergo a conversion which leads to green discolourations and to losses in whiteness levels.

To date, all high affinity fluorescent whitening agents have required a relatively low water-solubility, which has led immediately to the formation of a precipitate, e.g. the free acid form of the fluorescent whitening agent, at acidic pH values. On the other hand, stability in acidic baths could only be attained to date by using a fluorescent whitening agent having a higher water-solubility and, consequently, a lower affinity for the fibre.

Certain new diaminostilbene fluorescent whitening agents have now been found which, surprisingly, exhibit both a high affinity for cotton and an adequate stability in application baths having a pH value of 6 or below.

Accordingly, the present invention provides a compound having the formula:

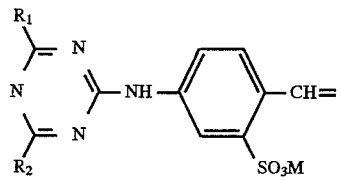

(1)

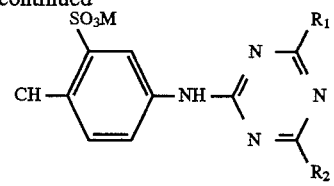

in which M is hydrogen, sodium, potassium, calcium, magnesium, ammonium, mono-, di-, tri- or tetra-$C_1$–$C_4$alkylammonium, mono-, di- or tri-$C_1$–$C_4$hydroxyalkylammonium or ammonium that is di- or tri-substituted by a mixture of $C_1$–$C_4$alkyl and $C_1$–$C_4$hydroxyalkyl groups; $R_1$ is a group having the formula:

in which M has its previous significance and n is 1 or 2, preferably 1; and $R_2$ is O—$C_1$–$C_{12}$alkyl or $N(R_3)(R_4)$ in which $R_3$ and $R_4$, independently, are hydrogen, $C_1$–$C_{12}$alkyl or $C_1$–$C_4$hydroxyalkyl, or $R_3$ and $R_4$, together with the nitrogen atom, are the atoms required to form a pyrrolidine, piperidine or morpholine group.

When M contains a $C_1$–$C_4$alkyl group, this may be, e.g., a methyl, ethyl, n-propyl, isopropyl or n-butyl group, but is preferably a methyl group.

When M contains a $C_1$–$C_4$hydroxyalkyl group, this may be, e.g., a hydroxymethyl, hydroxyethyl, hydroxy-n-propyl or hydroxy-n-butyl group, but is preferably a hydroxymethyl or hydroxyethyl group.

Preferably M is hydrogen or, especially sodium.

When $R_2$, $R_3$ or $R_4$ is or contains a $C_1$–$C_{12}$alkyl group, this may be, e.g., a methyl, ethyl, n-propyl, isopropyl, n-butyl, t-butyl, n-pentyl, n-hexyl, n-octyl, n-decyl or n-dodecyl group, but is preferably a $C_1$–$C_4$alkyl group, especially a methyl group.

A $C_1$–$C_4$hydroxyalkyl group $R_3$ or $R_4$ may be, e.g., a hydroxymethyl, hydroxyethyl, hydroxy-n-propyl or hydroxy-n-butyl group, but is preferably a hydroxymethyl or hydroxyethyl group or, especially, a 2-hydroxypropyl group —$CH_2CH(OH)CH_3$.

Preferably, $R_1$ is a group having the formula:

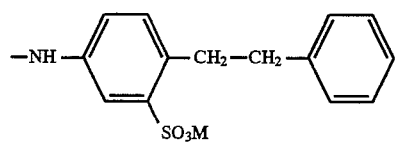

in which M has its previous significance.

Preferably, $R_2$ is a group of formula —$NR_3R_4$ in which $R_3$ and $R_4$, independently, are $C_1$–$C_4$alkyl or $C_1$–$C_4$hydroxyalkyl and particularly preferred compounds of formula (1) are those in which $R_3$ and $R_4$ are the same and each is $C_1$–$C_4$hydroxyalkyl, especially —$CH_2CH(OH)CH_3$.

A particularly preferred compound according to the present invention is that having the formula:

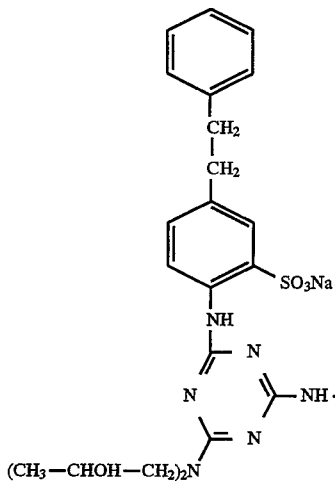

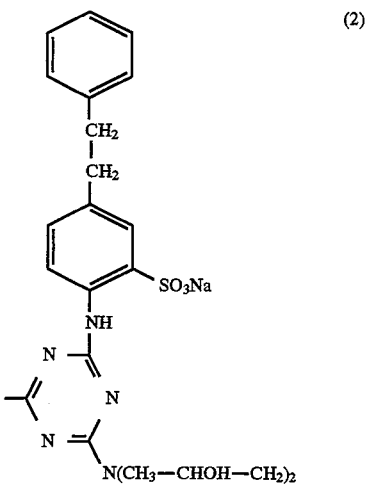

The compounds of formula (1) may be produced, e.g., by reacting cyanuric chloride, in any desired sequence, with the disodium salt of 4,4'-diaminostilbene-2,2'-disulfonic acid, the sodium salt of a compound having the formula:

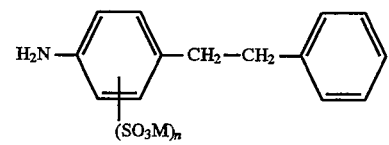

in which M and n have their previous significance, preferably 5-amino-2-(2-phenylethyl)-benzenesulfonic acid, and a compound capable of introducing a group $R_2$ into the triazine ring, namely a $C_1$–$C_{12}$ hydroxyalkyl compound or a compound $HNR_3R_4$, in which $R_3$ and $R_4$ have their previous significance.

The reactants are preferably used in substantially the stoichiometric proportions required to form the compounds of formula (1).

It is preferred to first condense cyanuric chloride, in the molecular ratio of substantially 2:1, with the disodium salt of 4,4'-diaminostilbene-2,2'-disulfonic acid. Subsequently, one chlorine atom in each of the two dichlorotriazine residues of the resulting intermediate of formula:

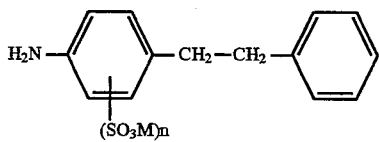

in which M and n have their previous significance, preferably the sodium salt of 5-amino-2-(2-phenylethyl)-benzenesulfonic acid. Finally, the two remaining chlorine atoms of the intermediate of formula:

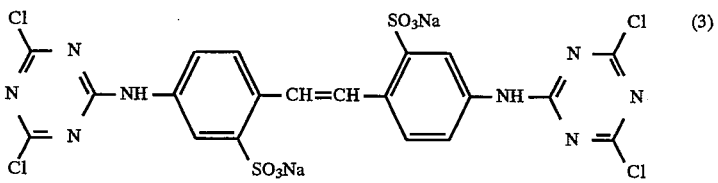

may be exchanged for the residue of the sodium salt of a compound having the formula:

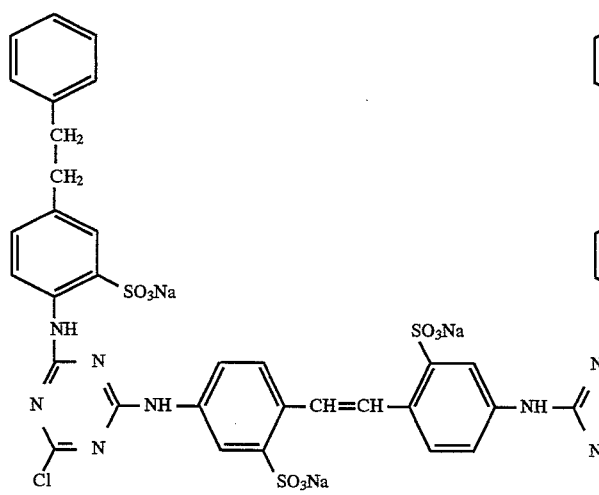
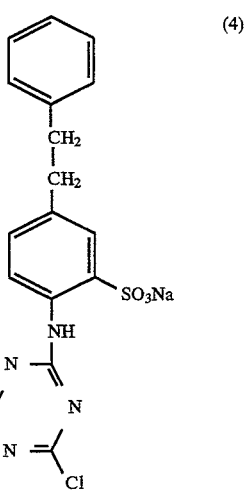

(4)

may be exchanged for the residue of the compound capable of introducing a group $R_2$ into the triazine ring and thereby obtain a compound of formula (1).

While the new fluorescent whitening agents of formula (1) may be used to whiten a wide variety of organic materials, using a wide range of application methods, as already indicated above, the new fluorescent whitening agents of formula (1) are particularly valuable for use in discontinuous processes for the whitening of cotton.

Accordingly, the present invention also provides a method for the fluorescent whitening of cotton in a discontinuous process comprising contacting the cotton, in an aqueous acidic bath, preferably an aqueous bath having a pH value of 6 or less, especially one having a pH value in the range of from 4 to 6, with one or more compounds having the formula (1).

Some of the compounds of formula (1) may be advantageously applied in dispersed form. For this purpose, they may be milled with an appropriate dispersant, conveniently using quartz balls and an impeller, down to a particle size of 1-2 microns.

As dispersing agents for such compounds there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;
polystyrene sulphonates;
fatty acid taurides;
alkylated diphenyloxide-mono- or -di-sulphonates;
sulphonates of polycarboxylic acid esters;
addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$–$C_6$alkanols, the addition products having been converted into an acid ester with an organic dicarboxylic acid or with an inorganic polybasic acid;
lignin sulphonates; and, in particular
formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

The compound of formula (1) may be used in the method of the present invention together with a minor proportion of one or more adjuvants. Examples of adjuvants include emulsifiers, perfumes, colouring dyes, opacifiers, bactericides, nonionic surfactants, anti-gelling agents such as nitrites or nitrates of alkali metals, especially sodium nitrate, and corrosion inhibitors such as sodium silicate.

The amount of each of these optional adjuvants is preferably within the range of from 0.01 to 1% by weight of the aqueous treatment bath.

The method of the present invention is usually conducted in the temperature range of from 20° to 140° C., for example at or near to the boiling point of the aqueous bath, e.g. at about 90° C.

The method of the present invention is conveniently conducted using an exhaust or foulard technique.

The method of the present invention may be combined with a textile treatment or finishing method.

It is often advantageous to use the compound of formula (1) in admixture with a minor amount of an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

The following Examples further illustrate the present invention.

EXAMPLE 1

A) Synthesis of the sodium salt of 5-amino-2-(2-phenylethyl)-benzenesulfonic acid having the formula:

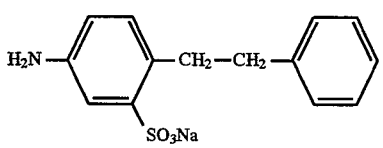

106 g of benzaldehyde and 241 g of the sodium salt of 4-nitrotoluene-2-sulfonic acid are condensed in dimethylformamide under Knoevenagel conditions for 24 hours at 130° C., using 20 g of piperazine as catalyst. 305 g (93% yield) are obtained of an orange compound having the formula:

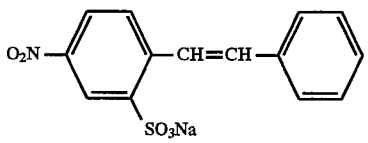

This orange compound is reduced, under Bechamp reaction conditions, to give an 84% yield of the corresponding amine of formula:

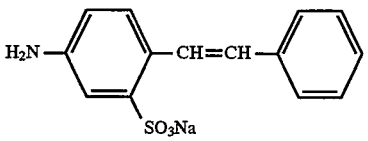

Finally, the amine is hydrogenated, using 5% Pd/C catalyst, in water at 25° C., to give an 88% yield of the sodium salt of 5-amino-2-(2-phenylethyl)-benzenesulfonic acid.

B) Synthesis of the compound having the formula:

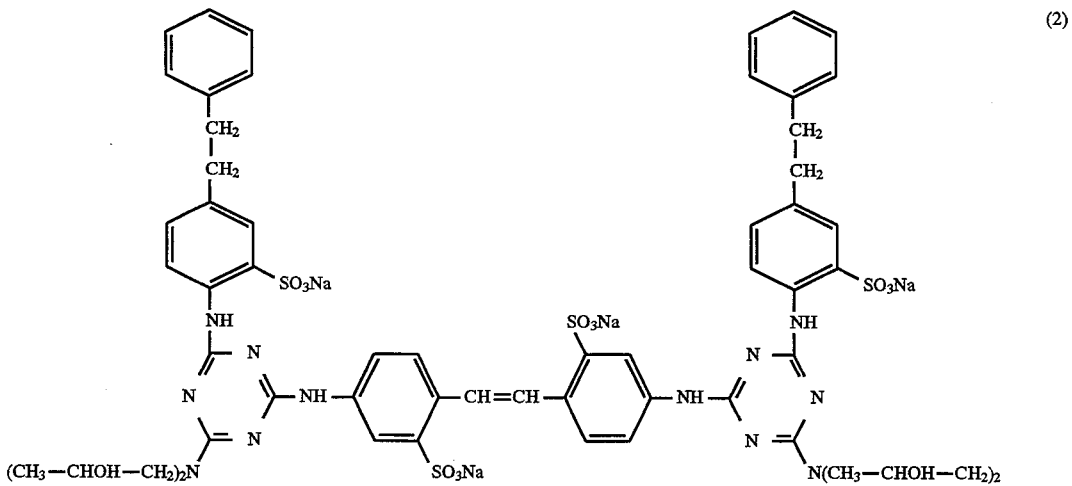

22 g of cyanuric chloride are stirred in 300 ml of acetone and 150 ml of water at −10° C. A solution of 22.2 g of 4,4'-diaminostilbene-2,2'-disulfonic acid in 100 ml of water is added over 30 minutes, followed by 60 ml of 1M soda solution.

The resulting mixture is stirred for 1 hour at −10° C. and then a solution of 35.9 g of the disodium salt of 5-amino-2-(2-phenylethyl)-benzenesulfonic acid in 150 ml of water is added at once, followed by 60 ml of 1M soda solution, and the temperature is increased to 20° C.

After stirring for 2 hours at this temperature, 60 g of di-isopropanolamine are added and stirring is continued at 50° C. for 4 hours.

The reaction mixture is cooled to 5° C. and the yellow precipitate is filtered off, washed with water and dried under vacuum at 100° C. The compound of formula (2) is obtained in a yield of 62% and has the following elemental analysis by weight:

Analysis for $C_{60}H_{64}N_{12}O_{16}S_4Na_4 \cdot 9.5H_2O \cdot 9.14NaCl$: Req.% C 33.84; H 3.90; N 7.89; S 6.00; $H_2O$ 7.98. Found % C 33.67; H 4.00; N 7.89; S 5.72; $H_2O$ 8.02.

EXAMPLE 2

Using the procedure described in Example 1, but replacing the di-isopropanolamine reactant by morpholine, the compound of formula:

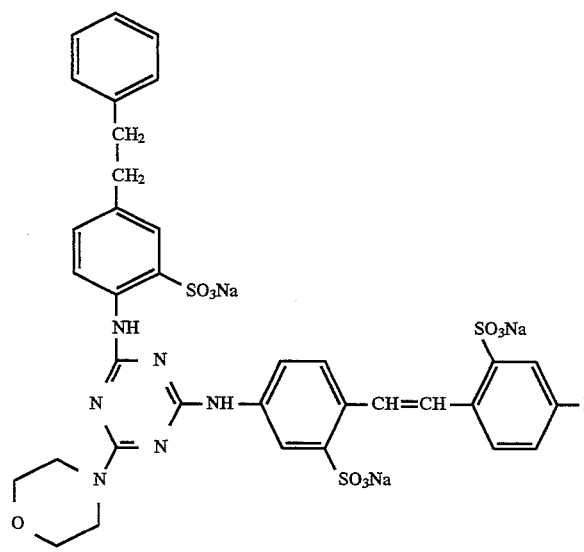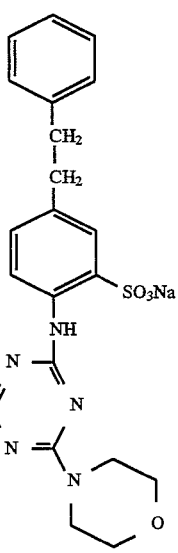

(5)

is obtained in a yield of 78% and has the following elemental analysis by weight:

Analysis for $C_{56}H_{52}N_{12}O_{14}S_4Na_4 \cdot 13H_2O$: Req.% C 41.81; H 5.00; N 10.67; S 8.16; $H_2O$ 14.71. Found % C 41.95; H 5.06; N 10.72; S 8.01; $H_2O$ 14.71.

EXAMPLE 3

Using the procedure described in Example 1, but replacing the di-isopropanolamine reactant by di-ethanolamine, the compound of formula:

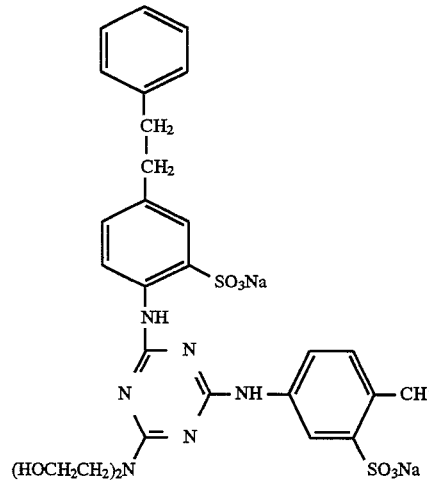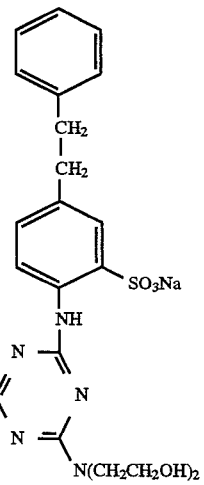

(6)

is obtained in a yield of 54% and has the following elemental analysis by weight:

Analysis for $C_{56}H_{56}N_{12}O_{16}S_4Na_4 \cdot 9.55H_2O \cdot 22.7NaCl$: Req. % C 23.42; H 2.62; N 5.85; S 4.46; $H_2O$ 6.20. Found % C 23.40; H 2.75; N 5.88; S 4.57; $H_2O$ 6.12.

Using the procedure described in Example 1, but replacing the di-isopropanolamine reactant by the appropriate amine, compounds of formula (1) in which $R_2$ is dimethylamino, diethylamino, piperidino or pyrrolidino are obtained.

EXAMPLE 4

Determination of fibre affinity

A) Various bleached cotton swatches are treated by the exhaust method in an aqueous bath having the following composition:

0.05% of test fluorescent whitener (100% active substance), based on weight of fibre; and 5 g/l of crystalline Glauber's salt.

The treatment is conducted at a liquor ratio of 1:20 for 15 minutes at 20°–50° C., and then for a further 15 minutes at 50° C. Finally, the respective treated swatches are removed from the treatment bath, rinsed and dried in conventional manner.

B) To determine the re-uptake of fluorescent whitener, the residual liquor from part (A) is treated with a further 5 g/l of crystalline Glauber's salt and fresh cotton swatches are treated by the exhaust method in the new aqueous bath for 20 minutes at 50° C. Finally, the respective treated swatches are removed from the treatment bath, rinsed and dried in conventional manner.

The whiteness levels (W) of the swatches obtained from the respective procedures A) and B) are determined by the Ganz method using a spectrophotometer.

The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The difference (ΔW) in whiteness level obtained in treatment A) or B) is taken as a measure of the affinity of the respective test fluorescent whitener for the test cotton fabric, a high ΔW value indicating high affinity for cotton, and vice versa.

The test fluorescent whiteners used are as follows:

a) the compound of the present invention having the formula (2);

b) a commercial fluorescent whitener having a high affinity for cotton and having the formula:

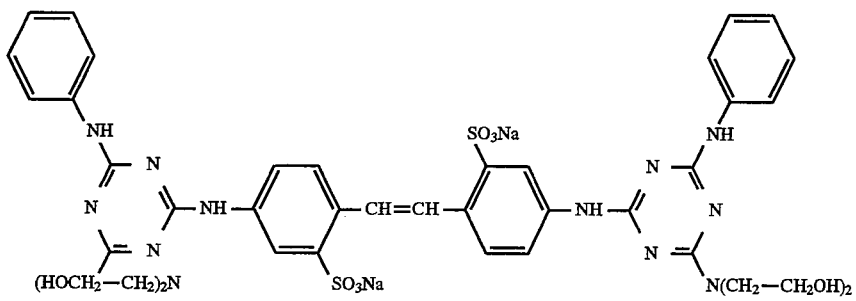
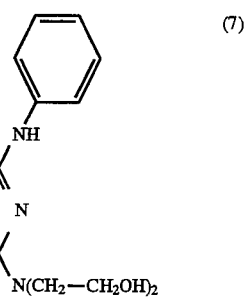

(7)

c) a commercial fluorescent whitener having an intermediate affinity for cotton and having the formula:

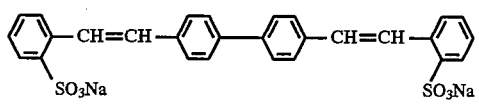

(8)

d) a commercial fluorescent whitener having a low affinity for cotton and having the formula:

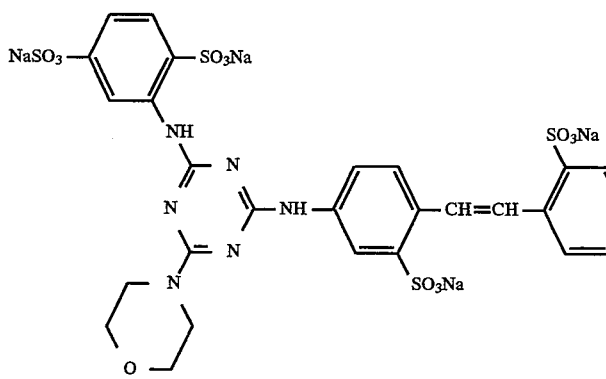
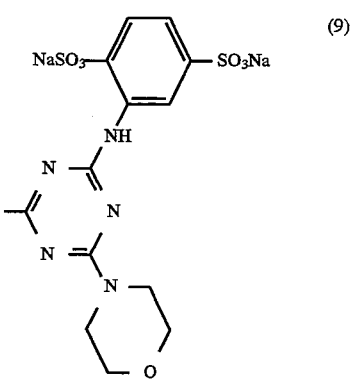

(9)

The results obtained are set out in the following Table.

TABLE 1

| Example | Test fluorescent whitening agent | ΔW |
|---|---|---|
| 1 | compound of formula (2) | 79 |
| — | compound of formula (7) | 99 |
| — | compound of formula (8) | 20 |
| — | compound of formula (9) | 0 |

The results in Table 1 clearly demonstrate that the compound of formula (2) of the invention is a fluorescent whitener having a high affinity for cotton.

EXAMPLE 5

Determination of pH stability

The sensitivity of the test fluorescent whitener to acidic pH values is evaluated in a bath and on the cotton fabric.

A solution containing 1 g/l of the test fluorescent whitener (as active substance) in drinking water (11 degrees of German hardness) is prepared, and separate samples of the solution are adjusted to different pH values and stored in the dark at 25° C.

The appearance of each sample is evaluated immediately, and also after 1, 2 and 4 hours after preparation.

After the respective 4 hour appearance evaluations, separate samples of bleached cotton are foularded with one of the respective solutions (liquor pick up about 70%). The respective fabric samples are dried at 70° C. for 20 minutes and their Ganz whiteness values are determined as described in Example 4.

The solution appearance and Ganz whiteness (W) values obtained are set out in the following Table.

TABLE 2

| Example | Test whitener | Time | pH 7 | pH 6 | pH 5 | pH 4 |
|---|---|---|---|---|---|---|
| 1 | compound of formula (2) | at once | clear | clear | clear | slightly opal |
| | | after 1 hour | clear | clear | slightly opal | slightly opal |
| | | after 2 hours | clear | clear | slightly opal | slightly opal |
| | | after 4 hours | clear | clear | slightly opal | slightly opal |
| | | W | 197 | 197 | 194 | 160 |
| — | compound of formula (7) | at once | clear | cloudy | cloudy | cloudy |
| | | after 1 hour | clear | cloudy | cloudy | cloudy |
| | | after 2 hours | clear | cloudy | cloudy | cloudy |
| | | after 4 hours | clear | cloudy | cloudy | cloudy |
| | | W | 199 | 166 | 156 | 96 |

In contrast to the conventional high affinity fluorescent whitener of formula (7), which shows turbity and a serious loss of whiteness level even at a pH value of 6, a solution containing a high affinity fluorescent whitener compound of formula (2) of the invention can still be considered to be stable and shows no significant loss of whiteness level even at pH 5.

We claim:

1. A compound having the formula:

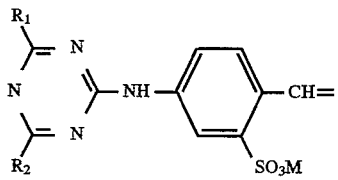

(1)

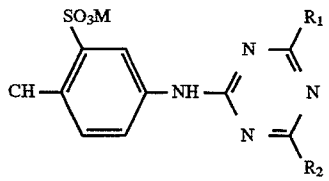

in which M is hydrogen, sodium, potassium, calcium, magnesium, ammonium, mono-, di-, tri- or tetra-$C_1$-$C_4$alkylammonium, mono-, di- or tri-$C_1$-$C_4$hydroxyalkylammonium or ammonium that is di- or tri-substituted by a mixture of $C_1$-$C_4$alkyl and $C_1$-$C_4$hydroxyalkyl groups; $R_1$ is a group having the formula:

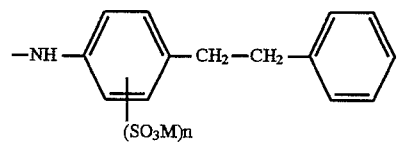

in which M has its previous significance and n is 1 or 2; and $R_2$ is O—$C_1$-$C_{12}$alkyl or $N(R_3)(R_4)$ in which $R_3$ and $R_4$, independently, are hydrogen, $C_1$-$C_{12}$alkyl or $C_1$-$C_4$hydroxyalkyl, or $R_3$ and $R_4$, together with the nitrogen atom, form a pyrrolidine, piperidine or morpholine group.

2. A compound according to claim 1 in which M is hydrogen or sodium.

3. A compound according to claim 1 in which n is 1.

4. A compound according to claim 1 in which $R_1$ is a group having the formula:

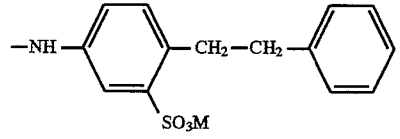

in which M is as defined in claim 1.

5. A compound according to claim 1 in which $R_2$ a group of formula —$NR_3R_4$ in which $R_3$ and $R_4$, independently, are $C_1$-$C_4$alkyl or $C_1$-$C_4$hydroxyalkyl.

6. A compound according to claim 5 in which $R_3$ and $R_4$ are the same and each is $C_1$-$C_4$hydroxyalkyl.

7. A compound according to claim 6 in which $R_3$ and $R_4$ are the same and each is —$CH_2$—$CH(OH)$—$CH_3$.

8. A compound according to claim 7 and having the formula:

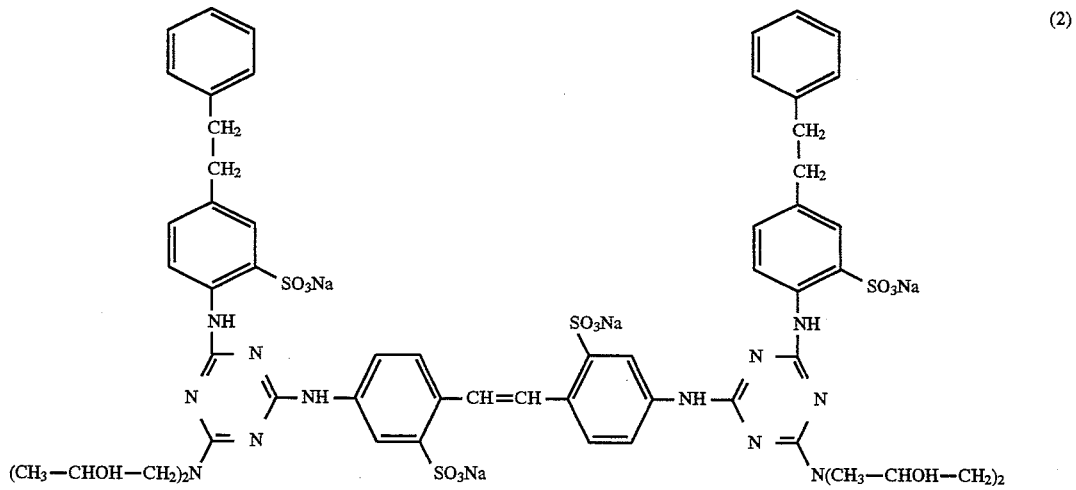

(2)

9. A process for the production of a compounds of formula (1) comprising reacting cyanuric chloride, in any desired sequence, with the disodium salt of 4,4'-diaminostilbene-2,2'-disulfonic acid, the sodium salt of a compound having the formula:

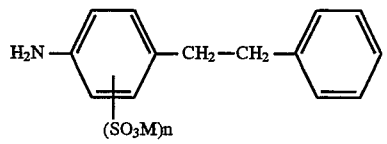

in which M and n are as defined in claim 1, and a compound capable of introducing a group $R_2$ into the triazine ring, namely a $C_1$–$C_{12}$ hydroxyalkyl compound or a compound $HNR_3R_4$, in which $R_2$, $R_3$ and $R_4$ are as defined in claim 1.

10. A process according to claim 9 comprising reacting cyanuric chloride, in any desired sequence, with the sodium salt of 5-amino-2-(2-phenylethyl)-benzenesulfonic acid and a compound capable of introducing a group $R_2$ into the triazine ring, namely a $C_1$–$C_{12}$ hydroxyalkyl compound or a compound $HNR_3R_4$, in which $R_2$, $R_3$ and $R_4$ are as defined in claim 1.

* * * * *